(12) United States Patent
Kath et al.

(10) Patent No.: US 6,673,801 B1
(45) Date of Patent: Jan. 6, 2004

(54) DIHYDROXYHEXANOIC ACID DERIVATIVES

(75) Inventors: John Charles Kath, Waterford, CT (US); Mathew Frank Brown, Pawcatuck, CT (US); Christopher Stanley Poss, North Stonington, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/403,218

(22) PCT Filed: Jan. 18, 1999

(86) PCT No.: PCT/IB99/00067

§ 371 (c)(1),
(2), (4) Date: Mar. 2, 2000

(87) PCT Pub. No.: WO99/40061

PCT Pub. Date: Aug. 12, 1999

Related U.S. Application Data

(60) Provisional application No. 60/073,801, filed on Feb. 5, 1998.

(51) Int. Cl.[7] .................. C07D 215/14; C07D 241/44; A61K 31/47; A61K 31/498; A61P 19/02
(52) U.S. Cl. .................. 514/255; 514/311; 544/355; 546/169
(58) Field of Search ............... 514/259, 311; 544/355; 546/169

(56) References Cited

U.S. PATENT DOCUMENTS 4,923,864 A    5/1990   Rosati .............. 514/234.8

FOREIGN PATENT DOCUMENTS

EP    0708085    4/1996

OTHER PUBLICATIONS

Ng, Howard, P. et al, J. Med. Chem., 42, 1999, 4680–4694.*
U.S. patent application Ser. No. 09/380,269, filed May 18, 2000.

* cited by examiner

Primary Examiner—Mukund J. Shah
Assistant Examiner—Thomas C McKenzie
(74) Attorney, Agent, or Firm—Peter C. Richardson; Gregg C. Benson; B. Timothy Creagan

(57) ABSTRACT

Dihydroxyhexanoic acid derivatives of the general formula

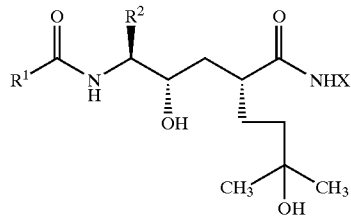

are useful to treat inflammation and other immune disorders.

3 Claims, No Drawings

DIHYDROXYHEXANOIC ACID DERIVATIVES

This application claims priority from provisional application No. 60/073,801, filed Feb. 5, 1998.

BACKGROUND OF THE INVENTION

The present invention relates to novel dihydroxyhexanoic acid derivatives, methods of use and pharmaceutical compositions containing them.

The compounds of the invention are potent and selective inhibitors of MIP-1α binding to its receptor CCR1 found on inflammatory and immunomodulatory cells (preferably leukocytes and lymphocytes). The CCR1 receptor is also sometimes referred to as the CC-CKR1 receptor. These compounds also inhibit MIP-1α (and the related chemokine shown to interact with CCR1 (e.g., RANTES and MCP-3)) induced chemotaxis of THP-1 cells and human leukocytes and are potentially useful for the treatment or prevention of autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult Respiratory Distress Syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), transplantation tissue rejection (chronic and acute), organ rejection (chronic and acute), atherosclerosis, restenosis, HIV infectivity (co-receptor usage), and granulomatous diseases (including sarcoidosis, leprosy and tuberculosis).

MIP-1α and RANTES are soluble chemotactic peptides (chemokines) which are produced by inflammatory cells, in particular CD8+ lymphocytes, polymorphonuclear leukocytes (PMNs) and macrophages, *J.Biol. Chem.*, 270 (30) 29671–29675 (1995). These chemokines act by inducing the migration and activation of key inflammatory and immunomodulatory cells. Elevated levels of chemokines have been found in the synovial fluid of rheumatoid arthritis patients, chronic and rejecting tissue transplant patients and in the nasal secretions of allergic rhinitis patients following allergen exposure (Teran, et al., *J. Immunol.*, 1806–1812 (1996), and Kuna et al., *J. Allergy Clin. Immunol.* 321 (1994)). Antibodies which interfere with the chemokine/receptor interaction by neutralizing MIP-1α or gene disruption have provided direct evidence for the role of MIP-1α and RANTES in disease by limiting the recruitment of monocytes and CD8+ lymphocytes (Smith et al., *J. Immunol*, 153, 4704 (1994) and Cook et al., *Science*, 269, 1583 (1995)). Together this data demonstrates that CCR1 antagonists would be an effective at treatment of several immune based diseases. The compounds described within are highly soluble, potent and selective antagonists of CCR1.

U.S. Pat. No. 4,923,864, issued May 8, 1990, refers to certain heterocyclic hexanamides that are useful for treating hypertension.

PCT publication WO 89/01488, published Feb. 23, 1989, refers to renin inhibiting peptides which possess nonpeptide linkages.

PCT publication WO 93/025057, published Feb. 4, 1993, refers to dipeptide analogs which are claimed to inhibit retroviral proteases.

PCT publication WO 93/17003, published Sep. 2, 1993 refers to other dipeptide analogs which are claimed to inhibit retroviral proteases.

PCT publication WO 92/17490, published Oct. 15, 1992, refers to peptides containing at least one O-phosphate monoester or diester. The compounds are claimed to possess activity for inhibiting retroviruses.

European Patent Publication 708,085, published Apr. 24, 1996, refers to antiviral ethers of aspartate protease inhibitors.

U.S. Provisional Patent Application No. 60/039169, filed Feb. 26, 1997, refers to other hexanoic acid derivatives which are also antagonists of the MIP-1α/RANTES interaction with CCR1.

SUMMARY OF THE INVENTION

The present invention relates to compounds of the formula I

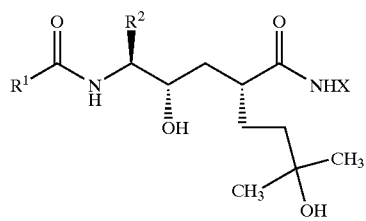

wherein said compound is:

quinoxaline-2-carboxylic acid 4(R)-carbamoyl-1(S)-(3-chloro-benzyl)-2(S),7-dihydroxy-7-methyl-octyl]-amide;

7,8-difluoro-quinoline-3-carboxylic acid (1S)-benzyl-4(R)-carbamoyl-2(S),7-dihydroxy-7-methyl-octyl)-amide;

6,7,8-trifluoro-quinoline-3-carboxylic acid (1(S)-benzyl-4(R)-carbamoyl-2(S),7-dihydroxy-7-methyl-octyl)-amide;

quinoxaline-2-carboxylic acid [4(R)-carbamoyl-1(S)-(3-fluoro-benzyl)-2(S),7-dihydroxy-7-methyl-octyl]-amide;

quinoxaline-2-carboxylic acid (1(S)-benzyl-2(S),7-dihydroxy-4(R)-hydroxycarbamoyl-7-methyl-octyl)-amide;

quinoxaline-2-carboxylic acid [4(R)-carbamoyl-1(S)-(2-chloro-benzyl)-2(S),7-dihydroxy-7-methyl-octyl]-amide;

quinoxaline-2-carboxylic acid [1(S)-(2-fluoro-benzyl)-2(S),7-dihydroxy-4(R)-hydroxycarbamoyl-7-methyl-octyl]-amide;

quinoxaline-2-carboxylic acid [4(R)-carbamoyl-1(S)-(2-fluoro-benzyl)-2(S),7-dihydroxy-7-methyl-octyl]-amide;

quinoxaline-2-carboxylic acid [1(S)-(3,4difluoro-benzyl)-2(S),7-dihydroxy-4(R)-hydroxycarbamoyl-7-methyl-octyl]-amide;

quinoxaline-2-carboxylic acid [4(R)-carbamoyl-1(S)-(3,4-difluoro-benzyl)-2(S),7-dihydroxy-7-methyl-octyl]-amide; or quinoxaline-2-carboxylic acid (4(R)-carbamoyl-2(S),7-dihydroxy-7-methyl-1(S)-naphthalen-1ylmethyl-octyl)-amide;

and pharmaceutically acceptable salts thereof.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The present invention also relates to a pharmaceutical composition for treating or preventing a disorder or condition selected from autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult respiratory distress syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), transplantation tissue rejection, atherosclerosis, restenosis, HIV infectivity (co-receptor usage), and granulomatous diseases (including sarcoidosis, leprosy and tuberculosis) in a mammal, preferably a human, comprising an amount of a compound of the formula I or a pharmaceutically acceptable salt thereof effective in treating or preventing such disorder or condition and a pharmaceutically acceptable carrier.

The present invention also relates to a pharmaceutical composition for treating or preventing a disorder or condition that can be treated or prevented by inhibiting MIP-1α binding to the receptor CCR1 in a mammal, preferably a human, comprising an amount of a compound of the formula I, or a pharmaceutically acceptable salt thereof, effective in treating or preventing such disorder or condition and a pharmaceutically acceptable carrier. Examples of such disorders and conditions are those enumerated in the preceding paragraph.

The present invention also relates to a method for treating or preventing a disorder or condition selected from autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult respiratory distress syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), transplantation tissue rejection, atherosclerosis, restenosis, HIV infectivity (co-receptor usage), and granulomatous diseases (including sarcoidosis, leprosy and tuberculosis) in a mammal, preferably a human, comprising administering to a mammal in need of such treatment or prevention an amount of a compound of the formula I, or a pharmaceutically acceptable salt thereof, that is effective in treating or preventing such disorder or condition.

The present invention also relates to a method for treating or preventing a disorder or condition that can be treated or prevented by antagonizing the CCRI receptor in a mammal, preferably a human, comprising administering to a mammal in need of such treatment or prevention an amount of a compound of the formula I, or a pharmaceutically acceptable salt thereof, that is effective in treating or preventing such disorder or condition.

The present invention also relates to a pharmaceutical composition for treating or preventing a disorder or condition selected from autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult respiratory distress syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), transplantation tissue rejection, atherosclerosis, restenosis, HIV infectivity (co-receptor usage), and granulomatous diseases (including sarcoidosis, leprosy and tuberculosis) in a mammal, preferably a human, comprising a CCR1 receptor antagonizing effective amount of a compound of the formula I, or a pharmaceutically acceptable salt thereof, and a pharmaceutically acceptable carrier.

The present invention also relates to a pharmaceutical composition for treating or preventing a disorder or condition that can be treated or prevented by antagonizing the CCR1 receptor in a mammal, preferably a human, comprising a CCR1 receptor antagonizing effective amount of a compound of the formula I, or a pharmaceutically acceptable salt thereof, and a pharmaceutically acceptable carrier.

The present invention also relates to a method for treating or preventing a disorder or condition selected from autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult respiratory distress syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), transplantation tissue rejection, atherosclerosis, restenosis, HIV infectivity (co-receptor usage), and granulomatous diseases (including sarcoidosis, leprosy and tuberculosis) in a mammal, preferably a human, comprising administering to a mammal in need of such treatment or prevention a CCR1 receptor antagonizing effective amount of a compound of formula I, or a pharmaceutically acceptable salt thereof.

This invention also encompasses pharmaceutical compositions containing and methods of treating or preventing comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain. Prodrugs also include compounds of formula I in which an amide nitrogen and a hydroxy group when taken together form a cyclic group such as the following formula

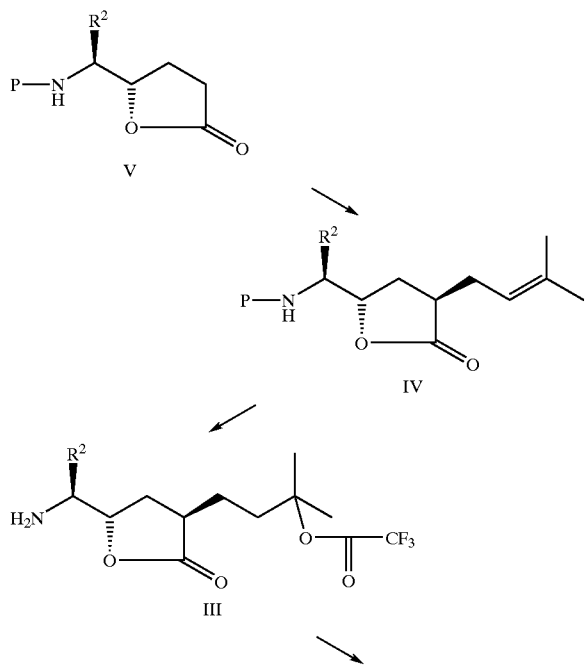

wherein $R^1$ and $R^2$ are as defined in formula I and U and V are independently carbonyl, methylene, $SO_2$ or $SO_3$, and b is an integer from one to three wherein each methylene group is optionally substituted with hydroxy.

DETAILED DESCRIPTION OF THE INVENTION

Compounds of the formula I may be prepared according to the following reaction Scheme and discussion.

SCHEME 1

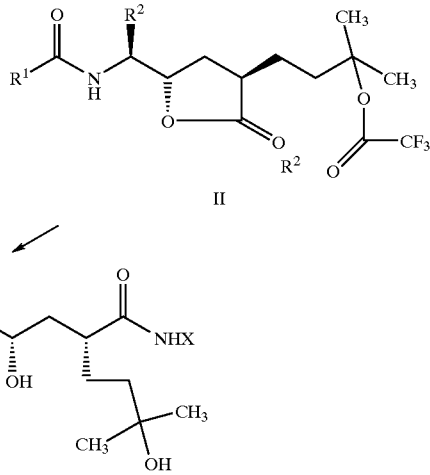

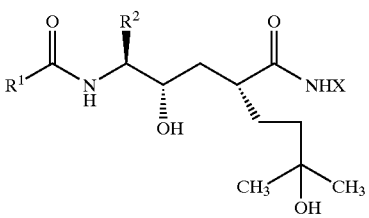

Scheme 1 refers to the preparation of compounds of the formula I having the exact stereochemistry

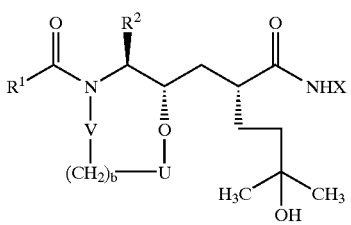

Compounds of the formula I, or any of the intermediates thereof, can be separated by column chromatography according to methods well known to those of ordinary skill in the art, to yield pure compounds of the formula I.

Referring to Scheme 1, compounds of the formula I, can be prepared from compounds of formula II by reaction with ammonia or another volatile low molecular weight amine in a polar solvent at a temperature from about −10° C. to about 35° C., preferably at about 30° C. Suitable solvents include, alcohols, such as methanol, ethanol, or butanols; or ethers such as glyme or dioxane (an acid catalyst may be used with an ether solvent). Preferably the solvent is methanol.

Compounds of formula II are prepared by coupling a compound of formula III with an acid of the formula $R^1CO_2H$ (or an acid chloride thereof wherein Ra is quinoxaline-2-carboxylic acid, 7,8 difluoro-quinoline-3-carboxylic-acid or 6,7,8-trifluoroquinoline-3-carboxylic acid). Such a coupling reaction is generally conducted at a temperature of about −30° C. to about 80° C., preferably about 0° C. to about 25° C. Examples of suitable coupling reagents which activate the carboxylic acid functionality are dicyclohexylcarbodiimide/hydroxybenzotriazole (DCC/HBT), N-3-dimethylaminopropyl-N'-ethylcarbodiimide (EDC)/HBT, 2-ethyoxy-1-ethoxycarbonyl-1,2-dihydroquinoline (EEDQ), carbonyl diimidazole (CDI)/dimethylaminopyridine (DMAP), and diethylphosphorylcyanide. The coupling is conducted in an inert solvent, preferably an aprotic solvent, such as acetonitirile, dichloromethane, chloroform, and dimethylformamide. The preferred solvent is dichloromethane.

For a discussion of other conditions used for amide coupling see Houben-Weyl, Vol. XV, part II, E. Wunsch, Ed., George Theime Veriag, 1974, Stuttgart, and those described in M. Bodanszky. *Principles of Peptide Synthesis,* Springer-Verlag, Berlin (1984) and *The Peptides, Analysis, Synthesis and Biology* (ed. E. Gross and J. Meienhofer), Vois 1–5. (Academic Press, New York) 1979–1983.

The compounds of formula III, can be prepared by deprotection and alkene hydrolysis of compounds of the formula IV by reaction with trifluoro acetic acid. Suitable protecting groups, of the formula P, include t-butoxycarbonyl.

Compounds of the formula IV, can be prepared by reaction of a compound of formula V with 4-bromo-2-methyl-2-butene, in the presence of a strong base in an aprotic polar solvent. Suitable bases include lithium dialkyl amides such as lithium N-isopropyl-N-cyclohexylamide LDA or potassium hydride. Suitable solvents include ethers (such as THF, glyme or dioxane) benzene or toluene, preferably THF. The aforesaid reaction is conducted at about –78° C. to about 0° C., preferably at about –78° C.

Compounds of the formula V can be prepared by methods well known to those of ordinary skill in the art or are commercially available. Specifically, compounds of the formula V can be prepared by the method of Fray et al., (*J. Org. Chem.*, 51, 4828–4833 (1986)) using an (S)-aldehyde of the formula

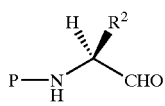

VII

Compounds of the formula VII are prepared by reducing amino acids or amino esters to alcohols (Stanfield et al., *J. Org. Chem.* 46, 4799–4800 (1981), Soai et al., *Bull. Chem. Soc. Jpn.*, 57, 2327 (1984)) followed by oxidation of the alcohols to aldehydes of the formula VII (Luly et al., *J.Org. Chem.*, 53 (26), 6109–4112 (1988) and Denis et al., *J Org. Chem.*, 56 (24), 6939–6942 (1991).). Un-natural amino acids can be prepared according to the method of Myers et al., *Tet. Lett.* 36, (1995) and Myers et al. *J. Am. Chem. Soc.*, 117, 8488–8489 (1995).

Alternatively, compounds of the formula V can also be made by the method of DeCamp et al., (*Tetrahedron Lett.*, 32, 1867 (1991)).

Unless indicated otherwise, the pressure of each of the above reactions is not critical. Generally, the reactions will be conducted at a pressure of about one to about three atmospheres, preferably at ambient pressure (about one atmosphere).

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Compounds of the formula I and their pharmaceutically acceptable salts (hereinafter also referred to, collectively, as "the active compounds") are potent antagonists of the CCR1 receptors. The active compounds are useful in the treatment or prevention of autoimmune diseases (such as rheumatoid arthritis, type I diabetes (recent onset), inflammatory bowel disease, optic neuritis, psoriasis, multiple sclerosis, polymyalgia rheumatica, uveitis, and vasculitis), acute and chronic inflammatory conditions (such as osteoarthritis, adult respiratory distress syndrome, Respiratory Distress Syndrome of infancy, ischemia reperfusion injury, and glomerulonephritis), allergic conditions (such as asthma and atopic dermatitis), infection associated with inflammation (such as viral inflammation (including influenza and hepatitis) and Guillian-Barre), transplantation tissue rejection, atherosclerosis, restenosis, HIV infectivity (co-receptor usage), and granulomatous diseases (including sarcoidosis, leprosy and tuberculosis).

The activity of the compounds of the invention can be assessed according to procedures know to those of ordinary skill in the art. Examples of recognized methods for determining CCR1 induced migration can be found in roligan, J. E., Kruisbeek, A. M., Margulies, D. H., Shevach, E. M., Strober, W. editors: *Current Protocols In Immunology,* 6.12.1–6.12.3. (John Wiley and Sons, NY, 1991). One specific example of how to determine the activity of a compound for inhibiting migration is described in detail below.

Chemotaxis Assay

The ability of compounds to inhibit the chemotaxis to various chemokines can be evaluated using standard 48 or 96 well Boyden Chambers with a 5 micron polycarbonate filter. All reagents and cells can be prepared in standard RPMI (BioWhitikker Inc.) tissue culture medium supplemented with 1 mg/ml of bovine serum albumin. Briefly, MIP-1α (Peprotech, Inc., P.O. Box 275, Rocky Hill N.J.) or other test agonists, were placed into the lower chambers of the Boyden chamber. A polycarbonate filter was then applied and the upper chamber fastened. The amount of agonist chosen is that determined to give the maximal amount of chemotaxis in this system (e.g., 1 nM for MIP-1α should be adequate).

THP-1 cells (ATCC TIB-202), primary human monocytes, or primary lymphocytes, isolated by standard techniques can then be added to the upper chambers in triplicate together with various concentrations of the test compound. Compound dilutions can be prepared using standard serological techniques and are mixed with cells prior to adding to the chamber.

After a suitable incubation period at 37 degrees centigrade (e.g. 3.5 hours for THP-1 cells, 90 minutes for primary monocytes), the chamber is removed, the cells in the upper chamber aspirated, the upper part of the filter wiped and the number of cells migrating can be determined according to the following method.

For THP-1 cells, the chamber (a 96 well variety manufactured by Neuroprobe) can be centrifuged to push cells off the lower chamber and the number of cells can be quantitated against a standard curve by a color change of the dye fluorocein diacetate.

For primary human monocytes, or lymphocytes, the filter can be stained with Dif Quik® dye (American Scientific Products) and the number of cells migrating can be determined microscopically.

The number of cells migrating in the presence of the compound are divided by the number of cells migrating in control wells (without the compound). The quotant is the % inhibition for the compound which can then be plotted using standard graphics techniques against the concentration of compound used. The 50% inhibition point is then determined using a line fit analysis for all concentrations tested. The line fit for all data points must have an coefficient of correlation (R squared) of >90% to be considered a valid assay.

All of the compounds of the invention that were tested had $IC_{50}$ of less than 25 μM, in the Chemotaxis assay.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation. The active compounds of the invention may also be formulated for sustained delivery.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insulator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., rheumatoid arthritis) is 0.1 to 1000 mg of the active ingredient per unit dose which could be administered, for example, 1 to 4 times per day.

Aerosol formulations for treatment of the conditions referred to above (e.g., rheumatoid arthritis) in the average adult human are preferably arranged so that each metered dose or "puff" of aerosol contains 20 μg to 1000 μg of the compound of the invention. The overall daily dose with an aerosol will be within the range 0.1 mg to 1000 mg. Administration may be several times daily, for example 2, 3, 4 or 8 times, giving for example, 1, 2 or 3 doses each time.

The active agents can be formulated for sustained delivery according to methods well known to those of ordinary skill in the art. Examples of such formulations can be found in U.S. Pat. Nos. 3,538,214, 4,060,598, 4,173,626, 3,119,742, and 3,492,397.

The compounds of the invention can also be utilized in combination therapy with other therapeutic agents such as with immunosuppressant agents such as cyclosporin A and FK-506, Cellcept®, rapamycin, leuflonamide or with classical anti-inflammatory agents (e.g. cyclooxygenase/lipoxegenase inhibitors) such as tenidap, aspirin, acetaminophen, naproxen and piroxicam, steroids including prednisone, azathioprine and biological agents such as OKT-3, anti IL-2 monoclonal antibodies (such as TAC),.

The compounds of the present invention possess unexpected solubility that could not be predicted based on U.S. Patent Application No. 60/039169, filed Feb. 26, 1997. Specifically, all of the compounds of the present invention have at least 13 fold better solubility than would be expected based on compounds from U.S. Provisional Application No. 60/039169. Specifically, quinoxaline-2-carboxylic acid (2(S)-hydroxy-6-methyl-4(R)-methylcarbamoyl-1(S)-naphthalen-2-ylmethyl-heptyl)-amide (Example 127), and N-1(S)-benzyl-4(R)-carbamoyl-7-fluoro-2(S)-hydroxy-7-methyl-octy)-5,6-dichloro-nicotinamide (Example 247) both have solubilities of less than 5 µg/mL when assayed according to the kinetic solubility assay described below.

The following Examples illustrate the preparation of the compounds of the present invention. Melting points are uncorrected. NMR data are reported in parts per million (δ) and are referenced to the deuterium lock signal from the sample solvent (deuteriochloroform unless otherwise specified). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Low Resolution Mass Spectra (LRMS) were recorded on either a Hewlett Packard 5989®, utilizing chemical ionization (ammonium), or a Fisons (or Micro Mass) Atmospheric Pressure Chemical Ionization (APCI) platform which uses a 50/50 mixture of acetonitrile/water with 0.1% formic acid as the ionizing agent. Room or ambient temperature refers to 20–25° C. All non-aqueous reactions were run under a if nitrogen atmosphere for convenience and to maximize yields. Concentration at reduced pressure means that a rotary evaporator was used. The names for the compounds of the invention were created by the Autonom 2.0 PC-batch version from Beilstein Informationssysteme GmbH (ISBN 3–89536–9764).

Solubility of the compounds was determined by a kinetic solubility assay such as described in *Advanced Drug Delivery Review*, 23, 3–25 (1997). One embodiment of the method described in *Advanced Drug Delivery Review*, 23, 3–25 (1997) is described below. One of ordinary skilled in the art will appreciate that solubitlity can be determined by many different methods.

Solubility of the compounds is determined at four fixed concentrations and is expressed as µg/mL. Solubility or insolubility is measured in phosphate buffer using a turbidometric plate reader by automated micro addition of a compound predissolved in DMSO. Solubilities at 50, 100, 200 and 250 or 100, 200, 400 and 500 micrograms/mL can be determined by predissolving 1 mg of compound in sufficient DMSO to reach an initial concentration of 20 or 40 µg/uL.

A spectramax 250 UV transparent 96 well microplate is filled with 200 uL of Stock pH 7 phosphate buffer solution. A series of 25 absorption readings in a 5 by 5 matrix at a wavelength of 492 nm are taken for each well in the microplate containing pH buffer alone. This scan is to be used as a "blank", and the raw optical dispersion (OD) values are used as a baseline.

Compounds in DMSO solution are then added (column wise) down the microplate. Up to twenty four samples are assayed with each compound being placed in four contiguous wells column wise. Each column of the microplate contains four concentrations of compound in ascending concentration and ascending row order (A–D), or row (E–H). The volume of DMSO stock added to each well ranges from 0.25 to 1.25% of the buffer well volume. The plate is then shaken for 20 minutes to allow for mixing.

| Row | µL Volume | µg compound in DMSO | % DMSO |
|-----|-----------|---------------------|--------|
| A   | 0.5       | 20                  | 0.25   |
| B   | 1.0       | 20                  | 0.50   |
| C   | 2.0       | 20                  | 1.00   |
| D   | 2.5       | 20                  | 1.25   |
| E   | 0.5       | 40                  | 0.25   |
| F   | 1.0       | 40                  | 0.50   |
| G   | 2.0       | 40                  | 1.00   |
| H   | 2.5       | 40                  | 1.25   |

After compound addition, a second scan consisting of a series of 25 absorption readings in a 5 by 5 matrix are taken for each well in the microplate at the same wavelength as the first blank scan. The raw compound OD values for each reading in the 5 by 5 matrix are subtracted from the corresponding "blank" values in the 5 by 5 matrix to provide the raw solubility OD data.

Data obtained from the Tecan SLT Spectra Image Reader is then analyzed using a Visual Basic computer program (or can be calculated manually according to methods well known to those of ordinary skill in the art), so as to provide solubility data for each compound. The compound is considered to be out of solution when the absorbance value is greater than three times the baseline value. All of the compounds of the invention had solubilities greater than 100 µg/mL.

Preparation 1

Method A

Allylic Alkylation

{1(S)-[4(R)-(3-METHYL-BUT-2-ENYL)-5-OXO-TETRAHYDRO-FURAN-2(S)-YL]-2-PHENYL-ETHYL}-CARBAMIC ACID TERT-BUTYL ESTER

To a flame dried round bottom flask under a nitrogen atmosphere was added tetrahydrofuran (40 mL) followed by 1,1,1,3,3,3-hexamethyldisilazane (8 mL, 37.8 mmol). The mixture was cooled to 0° C. and n-butyl lithium (14.5 mL of a 2.5 M solution in hexanes, 36.0 mmol) was added. The mixture was stirred for 15 minutes, then cooled to −78° C. in dry ice/acetone bath. {1(S)-[5-Oxo-tetrahydro-furan-2(S)-yl]-2-phenyl-ethyl}-carbamic acid tert-butyl ester (5 g, 16.4 mmol) (prepared by the method of Fray, *J. Org. Chem.,* (51) 4828 (1986)) dissolved in tetrahydrofuran (50 mL) was added dropwise via syringe and stirring continued for 30 minutes. A solution of 4-bromo-2-methyl-2-butene (2.07 mL, 18.0 mmol) in 40 mL of THF was added dropwise via syringe. Stirring was continued for 3 hours during which time the temperature rose to −60° C. The mixture was quenched by slow addition of saturated, aqueous ammonium chloride (25 mL). Upon warming to room temperature, the solution was diluted with ether (300 mL) and transferred to a separatory funnel. The organic phase was washed with saturated aqueous citric acid (2×100 mL), saturated aqueous sodium bicarbonate (NaHCO₃)(2×100 mL), and 100 mL brine. The organic layer was dried over magnesium sulfate (MgSO₄) and the solvent removed under reduced pressure. Thin layer chromatography in 1:2 hexane/diethyl ether (Et₂O) revealed product with an R$_f$ of 0.8. The resulting crude oil was chromatographed on silica gel (225 g) eluting with 2:1 hexanes/diethyl ether to provide 4.73 g (77%) of the title compound. TLC: 1:2 Hexanes/Et₂O R$_f$: 0.8. ¹H NMR (400 MHz, CDCl₃): δ7.27 ppm (5H, m), 5.02 (1H, b), 4.52 (1H, d, J=9.3 Hz), Hz), 3.98 (1H, dt, J=8.5, 7.8 Hz), 2.93 (2H, m), 2.88 (1H, b), 2.68 (1H, m), 2.41 (1H, m), 1.92 (1H, m), 1.65 (3H, s), 1.58 (3H, s), 1.37 (9H, s).

Method B

QUINOXALINE-2-CARBOXYLIC ACID 1(S)-BENZYL-4(R)-CARBAMOYL-2(S), 7-DIHYDROXY-7-METHYLOCTYL)-AMIDE

To the lactone from method A (100 mg, 0.27 mmol) was added neat trifluoroacetic acid (1 mL). The resulting solution was stirred for 1 h and the trifluoroacetic acid removed in vacuo. The remaining residue was solvated in methylene chloride (10 mL) and triethylamine (0.15 mL, 1.07 mmol). Quinoxalyl chloride (58 mg, 0.3 mmol) was added as a solid and the mixture stirred for 18 h. The mixture was transferred to a separatory funnel and washed with citric acid (2×10 mL), NaHCO3 (10 mL) and brine (10 mL). The organic layer was dried (MgSO4) and the solvents filtered. The filtrate was concentrated in vacuo and the resulting residue was chromatographed on silica gel (10 g) eluting with 2:1 hexanes:ethyl acetate to provide 99 mg of the quinoxaline amide. This material was solvated in MeOH and ammonia gas was bubbled in for 5 min. The resulting solution was stirred for 16 h and the solvent removed in vacuo. The remaining residue was recrystallized (methylene chloride/methanol/Hexanes) to provide the title compound (90 mg, 72%). 1H NMR (400 MHz, CD3OD): d 9.38 (1H, s), 8.21 (1H, dd, J=4.4, 2.5 Hz), 8.14 (1H, dd, J=4.4, 2.5 Hz), 7.93 (2H, m), 7.26 (2H, d, J=6.9 Hz), 7.17 (2H, t, J=7.1 Hz), 7.09 (1H, t, J=7.3 Hz), 4.30 (1H, m), 3.75 (1H, m), 3.03–2.98 (2H, m), 2.47 (1H, m), 1.77 (1H, m), 1.56 (2H, m), 1.4 (2H, m), 1.07 (6H, s).

EXAMPLE 1

QUINOXALINE-2-CARBOXYLIC ACID (4(R)-CARBAMOYL-2(S),7-DIHYDROXY-7-METHYL-1(S)-THIOPHEN-2-YLMETHYL-OCTYL)-AMIDE

To a flame dried round bottom flask under a nitrogen atmosphere was added tetrahydrofuran (5 mL) followed by 1,1,1,3,3,3-hexamethyldisilazane (0.78 mL, 3.7 mmol). The mixture was cooled to 0° C. and n-butyl lithium (1.4 mL of a 2.5 M solution in hexanes, 3.38 mmol) was added. The mixture was stirred for 15 minutes, then cooled to −78 ° C. in dry ice/acetone bath. {1(S)-[5-Oxo-tetrahydro-furan-2 (S)-yl]-2-thienyl-ethyl}carbamic acid tert-butyl ester (500 mg, 1.61 mmol) (prepared by the method of Fray, *J. Org. Chem.,* (51) 4828 (1986) using BOC-L-2-thienylalanine as a starting material) dissolved in tetrahydrofuran (6 mL) was added dropwise via syringe and stirring continued for 30 minutes. A solution of 4-bromo-2-methyl-2-butene (0.21 mL, 1.77 mmol) in 5 mL of THF was added dropwise via syringe. Stirring was continued for 3 hours during which time the temperature rose to −60° C. The mixture was quenched by slow addition of saturated, aqueous ammonium chloride. Upon warming to room temperature, the solution was diluted with ether and transferred to a separatory funnel. The organic phase was washed with saturated aqueous citric acid, saturated aqueous sodium bicarbonate (NaHCO₃), and brine. The organic layer was dried over magnesium sulfate (MgSO₄) and the solvent removed under reduced pressure. Thin layer chromatography in 2:1 hexane/diethyl ether (Et₂O) revealed product with an R$_f$ of 0.25. The resulting crude oil was chromatographed on silica gel eluting with 2:1 hexanes/diethyl ether to provide 450 mg (74%) of the lactone.

To the lactone from above (450 mg, 1.19 mmol) was added neat trifluoroacetic acid (4.5 mL). The resulting solution was stirred for 1 hour and the trifluoroacetic acid removed in vacuo. The resulting amine salt (100 mg, 0.34 mmol) was solvated in methylene chloride (15 mL) and triethylamine (0.2 mL, 1.34 mmol). Quinoxalyl chloride (71 mg, 0.37 mmol) was added as a solid and the mixture stirred for 18 hours. The mixture was transferred to a separatory funnel and washed with citric acid, NaHCO₃ and brine. The organic layer was dried (MgSO₄) and the solvents filtered. The filtrate was concentrated in vacuo and the resulting residue was chromatographed on silica gel eluting with 2:1 hexanes:ethyl acetate to provide 108 mg (71%) of the quinoxaline amide. This material was solvated in MeOH and ammonia gas was bubbled in for 5 minutes. The resulting solution was stirred for 16 hour and the solvent removed in vacuo. The remaining residue was recrystallized (methylene chloride/methanol/Hexanes) to provide the title compound (60 mg, 53%). Melting point (MP) 158–159. Low Resolution Mass Spectrum (LRMS) 471, 453, 436. Solubility greater than 250 mg/mL.

Table 1 refers to the preparation of compounds of the formula I by methods analogous to the methods of Preparation 1 and Example 1.

TABLE 1

| Example | IUPAC Name | Melting Point | LRMS | Solubility |
|---|---|---|---|---|
| 2 | Quinoxaline-2-carboxylic acid 4(R)-carbamoyl-1(S)-(3-chloro-benzyl)-2(S),7-dihydroxy-7-methyl-octyl)-amide | 161–163 | 499, 481, 464 | >100 μg/ml |
| 3 | 7,8-Difluoro-quinoline-3-carboxylic acid (1S)-benzyl-4(R)-carbamoyl-2(S),7-dihydroxy-7-methyl-octyl)-amide | 171–173 | 501, 484 | >250 μg/ml |
| 4 | Quinoxaline-2-carboxylic acid [4(R)-carbamoyl-1(S)-(3-fluoro-benzyl)-2(S),7-dihydroxy-7-methyl-octyl]-amide | 153–155 | 483, 465, 448 | >250 μg/ml |
| 5 | 6,7,8-Trifluoro-quinoline-3-carboxylic acid (1(S)-benzyl-4(R)-carbamoyl 2(S),7-dihydroxy-7-methyl-octyl)-amide | 185–188 | 519, 502 | >250 μg/ml |
| 6 | Quinoxaline-2-carboxylic acid (1(S)-benzyl-2(S),7-dihydroxy-4(R)-hydroxycarbamoyl-7-methyl-octyl)-amide | 108–110 | 482, 464, 447 | >250 μg/ml |
| 7 | Quinoxaline-2-carboxylic acid [4(R)-carbamoyl-1(S)-(2-chloro-benzyl)-2(S),7-dihydroxy-7-methyl-octyl]-amide | | 481, 464 | >250 μg/ml |
| 8 | Quinoxaline-2-carboxylic acid [1(S)-(2-fluoro-benzyl)-2(S),7- | 130–131 | 499 | >250 μg/ml |

TABLE 1-continued

| Example | IUPAC Name | Melting Point | LRMS | Solubility |
|---|---|---|---|---|
|  | dihydroxy-4(R)-hydroxycarbamoyl-7-methyl-octyl]-amide |  |  |  |
| 9 | Quinoxaline-2-carboxylic acid [4(R)-carbamoyl-1(S)-(2-fluoro-benzyl)-2(S),7-dihydroxy-7-methyl-octyl]-amide | 147–148 | 483 | >250 μg/ml |
| 10 | Quinoxaline-2-carboxylic acid [1(S)-(3,4-difluoro-benzyl)-2(S),7-dihydroxy-4(R)-hydroxycarbamoyl-7-methyl octyl]-amide | 150–153 | 517, 499, 466 | >200 μg/ml |
| 11 | Quinoxaline-2-carboxylic acid [4(R)-carbamoyl-1(S)-(3,4-difluoro-benzyl)-2(S),7-dihydroxy-7-methyl-octyl]-amide | 110–120 | 501, 483, 466 | >250 μg/ml |
| 12 | Quinoxaline-2-carboxylic acid (4(R)-carbamoyl-2(S),7-dihydroxy-7-methyl-1(S)-naphthalen-1-ylmethyl-octyl)-amide | 155–158 | 515, 497, 480 | >250 μg/ml |

What is claimed is:

1. A compound of the formula

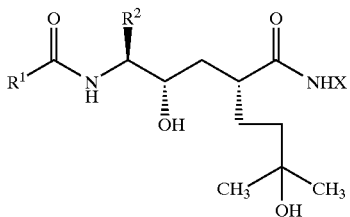

I wherein said compound is:
quinoxaline-2-carboxylic acid 4(R)-carbamoyl-1(S)-(3-chloro-benzyl)-2(S),7-dihydroxy-7-methyl-octyl]-amide;
7,8-difluoro-quinoline-3-carboxylic acid (1S)-benzyl-4(R)-carbamoyl-2(S),7-dihydroxy-7-methyl-otyl)-amide;
6,7,8-trifluoro-quinoline-3-carboxylic acid (1(S)-benzyl-4(R)-carbamoyl-2(S),7-dihydroxy-7-methyl-octyl)-amide;
quinoxaline-2-carboxylic acid [4(R)-carbamoyl-1(S)-(3-fluoro-benzyl)-2(S),7-dihydroxy-7-methyl-octyl]-amide;
quinoxaline-2-carboxylic acid (1(S)-benzyl-2(S),7-dihydroxy-4(R)-hydroxycarbamoyl-7-methyl-octyl)-amide;
quinoxaline-2-carboxylic acid [4(R)-carbamoyl-1(S)-(2-chloro-benzyl)-2(S),7-dihydroxy-7-methyl-octyl]-amide;
quinoxaline-2-carboxylic acid [1(S)-(2-fluoro-benzyl)-2(S),7-dihydroxy-4(R)-hydroxycarbamoyl-7-methyl-octyl]-amide;
quinoxaline-2-carboxylic acid [4(R)carbamoyl-1(S)-(2-fluoro-benzyl)-2(S),7-dihydroxy-7-methyl-octyl]-amide;
quinoxaline-2-carboxylic acid [1(S)-(3,4-difluoro-benzyl)-2(S),7dihydroxy-4(R)-hydroxycarbamoyl-7-methyl-octyl]-amide;
quinoxaline-2-carboxylic acid [4(R)-carbamoyl-1(S)-(3,4-difluoro-benzyl)-2(S),7-dihydroxy-7-methyl-octyl]-amide; or
quinoxaline-2-carboxylic acid (4(R)-carbamoyl-2(S),7-dihydroxy-7-methyl-1(S)-naphthalen-1-ylmethyl-octyl)-amide.

2. A pharmaceutical composition for treating a disorder or condition selected from multiple sclerosis or rheumatoid arthritis in a mammal, comprising an amount of a compound according to claim 1 that is effective in treating such disorder or condition and a pharmaceutically acceptable carrier.

3. A method for treating a disorder or condition selected from multiple sclerosis or rheumatoid arthritis in a mammal, comprising administering to a mammal in need of such treatment an amount of a compound according to claim 1, or a pharmaceutically acceptable salt thereof, that is effective in treating or preventing such disorder or condition.

* * * * *